(12) United States Patent
Dubey Pradip et al.

(10) Patent No.: US 10,023,548 B2
(45) Date of Patent: Jul. 17, 2018

(54) ENERGY EFFICIENT MANUFACTURING PROCESS FOR PREPARING N,O-TRIGLYCIDYL AMINOPHENOLS

(71) Applicant: Aditya Birla Chemicals (Thailand) Ltd., Bangkok (TH)

(72) Inventors: Kumar Dubey Pradip, Bangkok (TH); Alok Khullar, Bangkok (TH); Thipa Nayawat, Bangkok (TH); Kamonsun Visatsingh, Bangkok (TH); Patcharin Samuthsen, Bangkok (TH); Prashant Samant, Bangkok (TH)

(73) Assignee: Aditya Birla Chemicals (Thailand) Ltd., Bangkok (TH)

( * ) Notice: Subject to any disclaimer, the term of this patent is extended or adjusted under 35 U.S.C. 154(b) by 0 days.

(21) Appl. No.: 15/310,033

(22) PCT Filed: May 15, 2014

(86) PCT No.: PCT/TH2014/000024
§ 371 (c)(1),
(2) Date: Nov. 9, 2016

(87) PCT Pub. No.: WO2015/174936
PCT Pub. Date: Nov. 19, 2015

(65) Prior Publication Data
US 2017/0152236 A1    Jun. 1, 2017

(51) Int. Cl.
C07D 301/24    (2006.01)
C07D 303/36    (2006.01)

(52) U.S. Cl.
CPC ......... C07D 301/24 (2013.01); C07D 303/36 (2013.01)

(58) Field of Classification Search
CPC .................................. C07D 301/24; C07D 303/36
USPC ....................................................... 549/518
See application file for complete search history.

(56) References Cited

U.S. PATENT DOCUMENTS

| 2,951,825 A | | 9/1960 | Reinking et al. |
| 4,540,769 A | | 9/1985 | Dobinson et al. |
| 4,560,739 A | * | 12/1985 | Zahir .................... C07D 303/36 252/182.23 |
| 8,076,495 B2 | | 12/2011 | Malherbe et al. |

FOREIGN PATENT DOCUMENTS

| CN | 101139327 | | 3/2008 |
| JP | 02025474 | * | 1/1990 |
| JP | H04139230 | | 5/1992 |

OTHER PUBLICATIONS

Nakanishi; JPO Machine translation of JP 02025474 (Jan. 1990).*
Li; EPO Machine Translation of CN 101139327 (Mar. 2008).*

International Search Report and Written Opinion in International Application No. PCT/TH2014/000024.

* cited by examiner

Primary Examiner — Daniel R Carcanague
(74) Attorney, Agent, or Firm — Kim Winston LLP

(57) ABSTRACT

The invention relates to an improved process for making monomeric triglycidyl compounds, wherein the triglycidyl compounds include N, O-triglycidyl compounds containing at least one primary aromatic amine and one phenolic functional group attached to the same or a different aromatic ring. The methods of the present invention result in the production of N, O-triglycidyl compounds, such as those of formula I and II. The improved process is energy efficient, environment friendly, and results in increased yields of product. The methods of the present invention can be performed in the absence of protic organic co-solvents during the reaction of an epihalohydrin with an aminophenol, such as compounds of formula II and IV, which provides an intermediate halohydrin compound. The methods of the present invention may also be performed in the absence of a phase transfer catalyst.

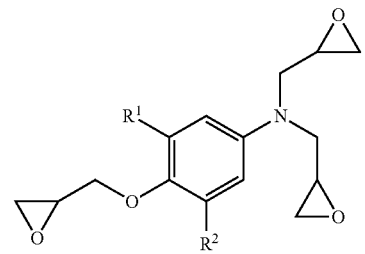

(I)

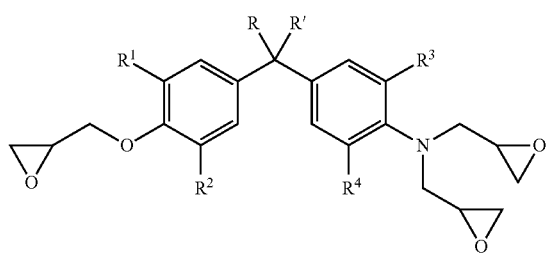

(II)

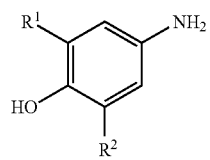

(III)

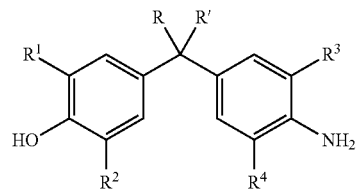

(IV)

20 Claims, No Drawings

ENERGY EFFICIENT MANUFACTURING PROCESS FOR PREPARING N,O-TRIGLYCIDYL AMINOPHENOLS

CROSS-REFERENCE TO RELATED APPLICATION

This application is a 371 of International Patent Application No. PCT/TH2014/000024 filed May 15, 2014, the entire disclosures of which is incorporated by reference herein in its entirety.

BACKGROUND OF INVENTION

Field of Invention

The present invention relates to an improved process for preparing N,O-triglycidyl aminophenol compounds. In one embodiment, the N,O-triglycidyl aminophenol compound is a compound of formula I or formula II, wherein R and R' are each independently selected from the group consisting of hydrogen, $C_1$-$C_6$ alkyl, phenyl, cyclohexyl and cyclopentyl, $R^1$, $R^2$, $R^3$, and $R^4$ are each independently selected from the group consisting of hydrogen, halogen, and $C_1$-$C_6$ alkyl. More particularly, the present invention is related to a process for preparing N,O-triglycidyl aminophenol compounds which does not require at least one polar protic organic co-solvent in the first step of the process, wherein the first step involves the formation of a halohydrin adduct by reaction of at least one epihalohydrin with at least one aminophenol. In one embodiment, the aminophenol is at least one compound of formula III or formula IV.

Using the methods of the current invention, separation of unreacted epihalohydrin, which is used in molar excess over the other reactants represented by structures III and IV, from a polar protic organic solvent, such as ethanol, isopropanol, n-butanol and the like, is no longer required because the process does not require the use of a polar protic organic solvent.

The methods of the current invention are economical and have fewer steps than currently used processes. More particularly, this disclosure relates to an industrially useful, energy efficient manufacturing process for the synthesis of triglycidyl compound from 4-amino phenols.

Triglycidyl aminophenols are commercially useful as high performance epoxy resins. They are versatile compounds, and are also used in structural adhesives and matrix resins for composites used in aviation, coatings, and insulation materials.

Because the properties of composites are dependent upon matrix resins, much effort has been placed into developing new resins while simultaneously improving processes for their manufacture.

The present invention relates to an improved manufacturing process for multifunctional epoxy resins of structures I and II. Multifunctional epoxies capable of forming higher cross linked structures are in demand both in military and civil applications. High temperature resistance and chemical resistance is function of crosslink density of a cured resin system. High cross link density can be achieved through multi-functionality on epoxy resin or hardener agent.

Description of Prior Art

For high performance applications which require epoxy resins with high heat distortion properties, such as in the aviation industry, resins having a glycidyl group bonded to a nitrogen atom of an aromatic amine functional group are often preferred, and several manufacturing processes of these types of compounds have been reported in prior art.

U.S. Pat. No. 8,076,495 B2 discloses a process which involves reacting aromatic amines with about 0.8-1.0 equivalents of epichlorohydrin per amino hydrogen atom. Compounds containing an aromatic amine group are dissolved in an organic solvent, such as toluene, and reacted with epichlorohydrin. This method uses an exotic catalyst, such as hydrated lanthanum nitrate to, form the halohydrin adduct. This step is followed by a cyclisation step using caustic aqueous solution in the presence of a phase transfer catalyst. During the workup, more organic co-solvent (i.e., toluene) is added to remove residual inorganic salt. This process, however, has several drawbacks, including use limited to only one N-glycidyl amine compound and employing an expensive catalyst in the adduct formation step as well as a phase transfer catalyst in the cyclisation step. The process also requires an additional distillation step in order to separate the toluene from the epichlorohydrin for recycling and reuse of the reagents.

U.S. Pat. No. 4,540,769 discloses the synthesis of aromatic N-glycidyl amines by treating an amine having at least one but preferably two or more aromatic amino hydrogen atoms, with epichlorohydrin in the presence of a metal salt, which acts as a catalyst.

Both U.S. Pat. No. 8,076,495 B2 and U.S. Pat. No. 4,540,769 are silent on the epoxidation of compounds such as aminophenols, which have both an amine and hydroxyl functional group attached to an aromatic ring.

Epoxy resins with both hydroxyl and amine functional groups attached to an aromatic ring facilitate formation of N,O glycidyl ethers, resulting in more versatile epoxy resins with desirable characteristics, such as high distortion properties.

U.S. Pat. No. 2,951,825 discloses a method for producing a N,O glycidyl amine type epoxy compound, wherein p-aminophenol is reacted with epichlorohydrin at 25° C. for a period of 137 hrs in the presence of lithium hydroxide monohydrate catalyst and a participating organic co-solvent, such as ethyl alcohol, as solvent. However, this process results in lower product yield and productivity, and requires an additional step to separate the co-solvent from the reaction mixture.

Many of the prior art preparations of triglycidylaminophenols involve the use of a variety of alcohols, such as n-butanol, sec-butanol, n-pentanol, n-hexanol and iso-propanol, as an organic co-solvent in the step of forming the chlorohydrins adduct. Both CN 101139327 and JP 59044372 disclose the reaction of p-aminophenol and m-aminophenol with epichlorohydrin in an alcohol at 55° C. for 5 hrs. Other processes, such as those disclosed in JP 55033410 and JP 04139230, require the use of a lithium salt or a phase transfer catalyst in order to facilitate the reaction. For example, isobutanol was used as a co-solvent for producing aminophenol triglycidyl compounds in the presence of lithium hydroxide monohydrate catalyst.

In addition, the procedures of the prior art are silent on the recovery of the co-solvent, as well as the recycling and/or disposal of the reaction components, such as the epihalohydrin used for epoxidation, the organic co-solvent, and any inorganic catalyst used in the processes.

Another drawback of the prior art processes is the ability to maintain batch to batch identity and quality of the recovered mixed solvents. Moreover, the prior art processes require an additional step of fractionating the organic co-solvents from the epihalohydrin, making these processes more energy intensive.

There is a need in the art for improved and energy-efficient manufacturing processes for preparing N,O-triglycidyl aminophenols. The present invention satisfies this need in the art.

BRIEF SUMMARY OF THE INVENTION

A method for producing a triglycidyl aminophenol from at least one amino phenol and at least one halohydrin is described. The method includes the steps of:

(i) reacting the at least one aminophenol with the at least one epihalohydrin in a polar solvent to produce a halohydrin compound in a reaction mixture;

(ii) reacting the halohydrin compound in the reaction mixture with at least one alkali metal hydroxide to form the triglycidyl aminophenol;

(iii) removing epihalohydrin from the reaction mixture;

(iv) adding an organic solvent and an aqueous solvent to the reaction mixture to form an organic layer and an aqueous layer;

(v) isolating the organic layer;

(vi) washing the organic layer with water, (vii) isolating the organic layer by removing the water by phase separation; and (viii) recovering the organic solvent from the organic layer to provide the triglycidyl aminophenol.

In one embodiment, the triglycidyl aminophenol is at least one compound of formula I and formula II:

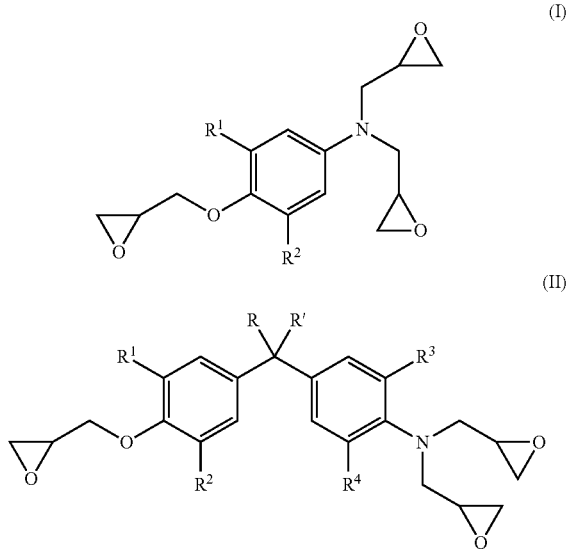

wherein:

$R^1$ and $R^2$ are each independently selected from the group consisting of hydrogen, halogen, or $C_1$-$C_6$ alkyl;

R and R' are each independently selected from the group consisting of hydrogen, $C_1$-$C_6$ alkyl, phenyl, cyclohexyl and cyclopentyl; and $R^1$, $R^2$, $R^3$, and $R^4$ are each independently selected from the group consisting of hydrogen, halogen, and $C_1$-$C_6$ alkyl; mixtures thereof and salts thereof.

In one embodiment, the aminophenol is the aminophenol is at least one compound of formula III and formula IV:

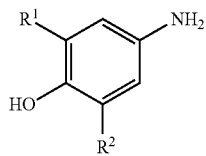

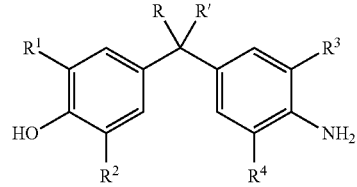

wherein:

$R^1$ and $R^2$ are each independently selected from the group consisting of hydrogen, halogen, or $C_1$-$C_6$ alkyl;

R and R' are each independently selected from the group consisting of hydrogen, $C_1$-$C_6$ alkyl, phenyl, cyclohexyl and cyclopentyl; and $R^1$, $R^2$, $R^3$, and $R^4$ are each independently selected from the group consisting of hydrogen, halogen, and $C_1$-$C_6$ alkyl; mixtures thereof and salts thereof.

In one embodiment, the epihalohydrin is at least one compound of formula V:

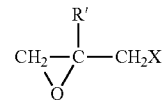

wherein in formula V:

R' is selected from the group consisting of hydrogen and methyl; and

X is selected from the group consisting of chlorine and bromine; and mixtures thereof.

In one embodiment, the polar solvent is water. In another embodiment, step (iii) further comprises removing the polar solvent. In another embodiment, the organic solvent of step (iv) is isolated and recycled without any additional purification. In another embodiment, in step (iii), the epihalohydrin is free of hydrolyzed byproducts. In another embodiment, in step (iii), the epihalohydrin is removed from the reaction mixture by distillation. In another embodiment, in step (vi), the organic solvent is recovered from the organic layer by distillation. In another embodiment, in step (vi), the organic layer is washed once with water. In another embodiment, in step (vi), the amount of water used for washing the organic layer is between about 0.5 mol to about 5 mol per mole of the at least one aminophenol. In another embodiment, the organic solvent is selected from the group consisting of an aromatic hydrocarbon or a cyclic fatty hydrocarbon. In another embodiment, the organic solvent is toluene or m-xylene. In another embodiment, steps (i)-(viii) are carried out in a batch process. In another embodiment, at least a portion of the organic solvent in step (vi) is used in step (iv) of a subsequent batch process. In another embodiment, at least a portion of the epichlorohydrin removed in step (iii) is used in step (i) of a subsequent batch process. In another embodiment, step (ii) is performed in the absence of a co-catalyst, further wherein the co-catalyst is selected from the group consisting of an external phase transfer catalyst and an onium salt compound. In another embodiment, the amount of at least one epihalohydrin is about 3 to about 5 moles per active hydrogen of the at least one aminophenol. In another embodiment, the amount of polar solvent is about 20% to about 70% by weight of the aminophenol. In another embodiment, steps (i) and (ii) are performed in the absence of any polar or non-polar organic solvents. In another embodiment, the at least one epihalohydrin is removed under reduced pressure. In another embodiment, the epihalohydrin is removed at a temperature below 90° C. In another embodiment, the chemical oxygen demand (COD) of the polar solvent is less than about 10,000 ppm. In another embodiment, the triglycidyl aminophenol is produced in a yield greater than about 98%. In another embodiment, the triglycidyl aminophenol has a hydrolysable halogen content less than about 400 ppm.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity, many other elements found in the art related to organic chemistry and the like. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Although any methods, materials and components similar or equivalent to those described herein can be used in the practice or testing of the present invention, the preferred methods and materials are described.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, ±5%, ±1%, or ±0.1% from the specified value, as such variations are appropriate to perform the disclosed methods.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "substituted" means that an atom or group of atoms has replaced hydrogen as the substituent attached to another group.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to an improved manufacturing process for producing monomeric triglycidyl aminophenols from at least one amino phenol and at least one halohydrin. In one embodiment, the monomeric triglycidyl aminophenol is a N,O-triglycidyl aminophenol. The methods of the present invention provide a more energy-efficient manufacturing process over those known in the prior art, as a polar protic organic co-solvent is not required in the first step of the method, which includes the formation of a halohydrin adduct of at least one aminophenol. Also, a phase transfer catalyst is not required for the cyclization reaction in the second step of the method, which includes the formation of the triglyceride aminophenol. Therefore, both the halohydrin adduct and the triglyceride aminophenol, as well as any waste water generated during the reaction steps, are free from contamination by inorganic catalysts, such as lithium salts, or phase transfer catalyst. The methods of the present invention provide an improved, high-yielding, environmentally-friendly manufacturing process for the preparation of triglycidyl aminophenol ethers using inexpensive and readily available reagents.

The methods of the present invention have many advantages over production methods currently known in the art. The present invention provides a green manufacturing process for producing triglycidyl aminophenols in the absence of protic organic solvents, such as ethanol or isopropanol, and in the absence of a phase transfer catalysts or co-catalyst based on inorganic salts of any type. The methods of the present invention provide a robust manufacturing process by reducing the number of steps necessary to produce triglycidyl aminophenols, resulting in a more energy efficient process that requires less time and a reduction in the amount of wastewater produced. These methods also improve the batch to batch identity of recovered epihalohydrin, organic solvents, and product, while reducing the loss of epihalohydrin, thereby enhancing the production efficiency and reducing production costs. In some embodiments, the yield of triglycidyl aminophenols is greater than about 98% mole/mole on the basis of aminophenol.

Methods

The present invention includes a method for producing a triglycidyl aminophenol from at least one amino phenol and at least one halohydrin.

In one embodiment, the triglyceride aminophenol is at least one compound of formula I and formula II:

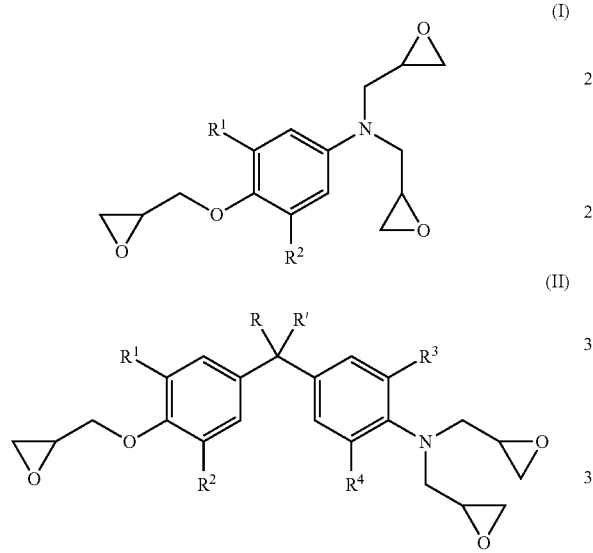

wherein:

$R^1$ and $R^2$ are each independently selected from the group consisting of hydrogen, halogen, or $C_1$-$C_6$ alkyl;

R and R' are each independently selected from the group consisting of hydrogen, $C_1$-$C_6$ alkyl, phenyl, cyclohexyl and cyclopentyl; and $R^1$, $R^2$, $R^3$, and $R^4$ are each independently selected from the group consisting of hydrogen, halogen, and $C_1$-$C_6$ alkyl; mixtures thereof and salts thereof.

In one embodiment, the method of the present invention comprises the step of reacting at least one aminophenol with at least one epihalohydrin in at least one polar solvent to produce a halohydrin compound in a reaction mixture. The halohydrin compound may be produced through a ring opening addition reaction between the at least one aminophenol and the at least one epihalohydrin. The ring-opening addition reaction is an exothermic reaction. In one embodiment, the step of reacting at least one aminophenol with at least one epihalohydrin is performed in the absence of any polar or non-polar organic solvent. Any aminophenol which is capable of reacting with an epihalohydrin is useful in the present invention, as would be understood by one skilled in the art.

In one embodiment, the aminophenol is at least one compound of formula III and formula IV:

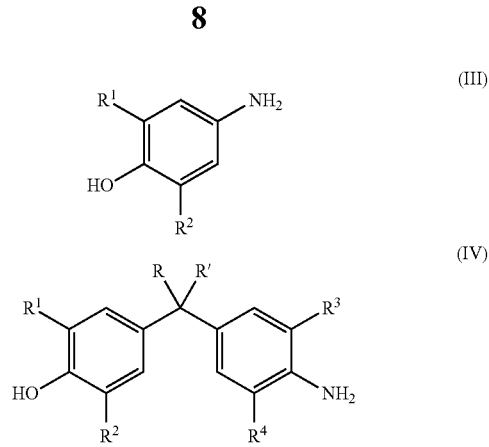

wherein:

$R^1$ and $R^2$ are each independently selected from the group consisting of hydrogen, halogen, or $C_1$-$C_6$ alkyl;

R and R' are each independently selected from the group consisting of hydrogen, $C_1$-$C_6$ alkyl, phenyl, cyclohexyl and cyclopentyl; and $R^1$, $R^2$, $R^3$, and $R^4$ are each independently selected from the group consisting of hydrogen, halogen, and $C_1$-$C_6$ alkyl; mixtures thereof and salts thereof.

In one embodiment, the aminophenol is selected from the group consisting of 4-aminophenol, 2-(4'-hydroxyphenyl)-2-(4'-aminophenyl)propane, and 4-(4-aminobenzyl)phenol, mixtures thereof and salts thereof.

In one embodiment, the halohydrin is at least one compound of formula V:

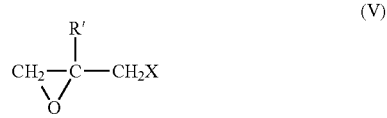

wherein in formula V:

R' is selected from the group consisting of hydrogen and methyl; and

X is selected from the group consisting of chlorine and bromine; and mixtures thereof.

In one embodiment, the epihalohydrin is selected from the group consisting of epichlorohydrin, epibromohydrin, β-methylepichlorohydrin, and mixtures thereof. In other embodiments, the epihalohydrin may be derived from natural sources like glycerol.

Any polar solvent which promotes the reaction between an aminophenol and an epihalohydrin is useful in the present invention, as would be understood by one skilled in the art. In one embodiment, the polar solvent is an aqueous solvent. In a preferred embodiment, the polar solvent is water.

In one embodiment, the amount of polar solvent employed in the reaction may range from about 20% to about 100% by weight of the aminophenol. In another embodiment, the amount of polar solvent is about 20% to about 70% by weight of the aminophenol. In another embodiment, the amount of polar solvent employed in the reaction is about 60% to about 70% by weight of the aminophenol. In some embodiments, an amount of water about 50% by weight of the aminophenol or greater promotes the ring opening addition reaction and prevents precipitation of reagents in the reaction mixture.

Stoichiometrically, 3 moles of epihalohydrin is required for 1 mole of aminophenol. Because the epihalohydrin serves as both a reactant and as a solvent in first step, the epichlorohydrin may be employed in a stoichiometric excess. In one embodiment, a stoichiometric excess of epihalohydrin is used. In one embodiment, the amount of epihalohydrin is from about 3.5 to about 7 moles per active hydrogen of aminophenol. In another embodiment, the amount of epihalohydrin is from about 3 to about 5 moles per active hydrogen of aminophenol. In one embodiment, the amount of epihalohydrin is from about 5 to about 30 moles per mole of aminophenol with three active hydrogens. In another embodiment, the amount of epihalohydrin is from about 9 to about 15 moles per mole of aminophenol with three active hydrogens.

It was found that when the amount of epihalohydrin is 10 moles or more per mole of aminophenol with three active hydrogens, increase in the viscosity of finished product can be controlled, while when the amount of epihalohydrin is 30 moles or less per mole of aminophenol with three active hydrogens, more of the space in the reactor can be utilized, thereby reducing the cost to recover unreacted epihalohydrin, which is economically advantageous. It was also found that when the amount of epihalohydrin is 3.5 moles or more per active hydrogen of aminophenol, the viscosity of the reaction mixture does not increase, while when the amount of epihalohydrin is 3 moles or less per active hydrogen of aminophenol, more of the space in the reactor can be utilized, thereby reducing the cost to recover unreacted epihalohydrin, which is economically advantageous.

The reaction may be performed at any suitable temperature, and for any suitable length of time. In one embodiment, the reaction is performed at a temperature ranging from about 40° C. to about 60° C. In another embodiment, the reaction is performed at a temperature ranging from about 40° C. to about 55° C.

In one embodiment, an aqueous slurry of the aminophenol and epichlorohydrin are heated to a temperature of about 45° to about 60° C., resulting in dissolution of the reactants. Preferably, the first step is performed in the absence of a polar protic organic solvent.

The method of the present invention may further comprise the step of reacting the halohydrin compound in the reaction mixture with at least one alkali metal hydroxide to form a triglycidyl aminophenol. This step results in an intramolecular cyclization reaction of the halohydrin compound to provide the triglycidyl aminophenol in a solution of epichlorohydrin. In one embodiment, the step of reacting the halohydrin compound in the reaction mixture with at least one alkali metal hydroxide is performed in the absence of any polar or non-polar organic solvent.

Any alkali metal hydroxide which promotes the cyclization reaction of the halohydrin compound is useful in the present invention, as would be understood by one skilled in the art. Examples of the alkali metal hydroxide are hydroxides of lithium, sodium potassium, rubidium and other metals in Group I of the periodic table. One or more kinds thereof can be used. In one embodiment, the alkali metal is sodium hydroxide. In one embodiment, the alkali metal is added to the reaction mixture as an aqueous solution. In one embodiment, the step is performed in the absence of a co-catalyst.

In another embodiment, the temperature of the reaction mixture during the addition of the alkali metal hydroxide to the reaction mixture is maintained at a temperature no greater than about 65° C. In one embodiment, the reaction is performed at a temperature no greater than about 65° C. In another embodiment, the temperature of the reaction mixture during the addition of the alkali metal hydroxide to the reaction mixture is maintained at a temperature of about 55° C. to about 65° C.

In one embodiment, the pressure of the reaction mixture during the addition of the alkali metal hydroxide to the reaction mixture is maintained at a pressure of about 150 mbar to about 220 mbar.

The reaction may be performed for any suitable length of time, which may vary depending upon the amount of the alkali metal hydroxide used. In one embodiment, the reaction has a reaction time ranging from 0.5 hours to 5 hours. In another embodiment, the reaction has a reaction time ranging from 1 to 3 hours.

In another embodiment, the step of removing epihalohydrin from the reaction mixture may further comprise removing the polar solvent. Removal of the polar solvent simultaneously as removal of the epihalohydrin produces a reaction mixture comprising triglycidyl aminophenol. The mixture of the epihalohydrin and solvent is an azeotrope, thereby allowing both solvent and epihalohydrin to be removed from the reaction mixture concurrently. In one embodiment, the chemical oxygen demand (COD) of the polar solvent is less than about 10,000 ppm.

The method of the present invention may further comprise the step of removing epihalohydrin from the reaction mixture. This step allows for the recovery of unreacted epihalohydrin while also ensuring complete removal of epihalohydrin from the reaction mixture and providing concentrated crude triglycidyl aminophenol and alkali metal halide produced during the cyclization reaction. The epihalohydrin can be removed from the reaction mixture using any known methods known in the art. In one embodiment, the epihalohydrin is removed from the reaction mixture under reduced pressure. Reduced pressure may include under vacuum. In one embodiment, the epihalohydrin is removed under reduced pressure. In one embodiment, the epihalohydrin is removed at a temperature below 100° C. In another embodiment, the epihalohydrin is removed at a temperature below 90° C. In another embodiment, the epihalohydrin is removed from the reaction mixture by distillation. In one embodiment, the removed epihalohydrin is recovered. In one embodiment, the epihalohydrin is free of hydrolyzed byproducts.

The method of the present invention may further comprise the step of adding an organic solvent and an aqueous solvent to the reaction mixture to form an organic layer and an aqueous layer. In one embodiment, the organic solvent is a non-polar organic solvent. Any non-polar organic solvent is contemplated for use in the invention. Non-limiting examples include toluene, m-xylene, benzene, hexanes, and the like. In one embodiment, the organic solvent is selected from the group of toluene and m-xylene, and combinations thereof. In another embodiment, the organic solvent is an aromatic hydrocarbon or a cyclic fatty hydrocarbon. In one embodiment, the aqueous solvent is water. The organic solvent will dissolve the crude triglycidyl aminophenol, producing an organic layer, while the aqueous solvent will dissolve alkali metal hydroxide and alkali metal halide salt, producing an aqueous layer. This step may further comprise the step of isolating the organic layer. In one embodiment, the organic layer is isolated by removing the aqueous layer by phase separation. The method may further comprise the step of washing the isolated organic layer with water. In one embodiment, the organic layer is washed once with water. In another embodiment, the amount of water used for washing the organic layer is between about 0.5 mol to about 5 mol per mole of aminophenol. In one embodiment, the organic layer is isolated from the water by phase separation.

In one embodiment, the amount of the organic solvent ranges from about 30 wt % to about 50 wt % of crude triglycidylaminophenol. In another embodiment, the amount of the organic solvent is about 40 wt % of crude triglycidylaminophenol.

The method of the present invention may further comprise the step of separating the organic solvent from the organic layer to provide the triglycidyl aminophenol. The organic solvent can be separated from the organic layer using any known methods known in the art. In one embodiment, the organic solvent is separated by distillation. In another embodiment, the organic solvent is separated by fractionation. This step allows for isolating and subsequently recycling the organic solvent, while also permitting isolation of the triglycidyl aminophenol. In one embodiment, the separated organic solvent is isolated and recycled without additional purification.

Recovery of the organic solvent may be performed at any suitable temperature. In one embodiment, recovery of the organic solvent may be performed at a temperature no greater than about 100° C. In another embodiment, recovery of the organic solvent may be performed at a temperature no greater than about 90° C.

In one embodiment, the steps of the method of the present invention are carried out in a batch process. In a further embodiment, epihalohydrin recovered from the reaction mixture is recycled without further purification, and at least a portion of the epihalohydrin is used in the step of reacting at least one aminophenol with at least one epihalohydrin in a subsequent batch process. In another embodiment, the organic solvent recovered from the organic layer is recycled without further purification, and at least a portion of the organic solvent is used in the step of adding an organic solvent and an aqueous solvent to the reaction mixture in a subsequent batch process.

The triglycidyl aminophenol produced using the methods of the present invention has a desired low viscosity, low hydrolysable halogen content and low residual epihalohydrin content. In one embodiment, the triglycidyl aminophenol has a viscosity ranging from about 28 to about 29 pascals. In one embodiment residual epihalohydrin content of less than about 100 ppm. In one embodiment, the triglycidyl aminophenol has a hydrolysable halogen content of about 600 ppm or less. In another embodiment, the triglycidyl aminophenol has a hydrolysable chlorine content of less than about 400 ppm. The methods of the present invention also provide high yields of triglycidyl aminophenol. In one embodiment, the yield of triglycidyl aminophenol is greater than about 98%. In another embodiment, the yield of triglycidyl aminophenol ranges from about 93% to about 95%.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1

Epichlorohydrin (507.3 g, 5.48 moles), water (42.35 g, 2.35 moles,) and p-aminophenol (60.5 g, 0.6 mole) were added in 1-L 4 neck flask with condenser and a stirrer. The temperature of the reaction mixture was elevated to 40° C., under the nitrogen atmosphere. The reaction temperature was maintained at 40° C. for 5 hours, to complete halohydrin adduct formation.

Subsequently, the temperature of halohydrin adduct was raised to 60° C. followed by addition of 50% w/w aqueous sodium hydroxide solution (119.7 g) at a constant flow rate in 3-4 hrs under 180 mbar pressure, the water was removed with epichlorohydrin from the reaction solution azeotropically.

To isolate crude halohydrin adduct, unreacted epichlorohydrin was recovered by distillation at 90° C./20 mbar.

Water (262.5 g, 14.6 moles) was added to the crude triglycidyl aminophenol to dissolve alkali salt produced during cyclization reaction. Toluene (163.2 g, 1.7 moles) was metered for dissolving crude triglycidylaminophenol followed by the phase separation. Waste water containing sodium chloride was removed in order to isolate the organic layer.

The organic layer was subjected to distillation under reduced pressure (90° C./20 mbar). The product was refined to suitable hydrolysable halogen content to get product with 99.7% purity, 0.05% epichlorohydrin content. The triglycidyl aminophenol was filtered, resulting in a 95% yield, viscosity at 25° C. of 35 Ps, 108.5 g/eq and hydrolysable halogen content 840 ppm.

Examples 2 to 4

The procedure of Example 1 was repeated, except that mole ratio of epichlorohydrin was changed as shown in Table 1, to thereby produce triglycidylaminophenol compound.

Comparative Example 1 p-Aminophenol (24.4 g, 0.22 moles), isopropanol (138 g, 40% weight of epichlorohydrin) and epichlorohydrin (206.8 g, 2.23 moles) were added to a 1-L 4 flask, and stirred. The temperature of the reaction mixture was elevated to 55° C. under the nitrogen atmosphere for 5 hours, for the addition reaction leading to halohydrin formation. The 50% w/w aqueous sodium hydroxide solution (54.5 g, 0.68 moles) was added to the reaction mixture at 55° C. at a constant rate over 1 to 1½ hours. The reaction temperature was further maintained at 55° C. for one hour, to allow cyclization reaction completely. Water (119.4 g, 6.6 moles) was added to the reaction mixture, to thereby dissolve sodium chloride the byproduct, formed during reaction. After the phase separation of aqueous salt containing layer, excess epichlorohydrin and isopropanol solvent were removed through evaporation under reduced pressure at 90° C./20 mbar to obtain tri glycidylether of p-amino phenol. The yield of the product after refining was 92-94% mole/mole over 4-amino phenol, viscosity at 25° C. of 25.5 Ps, 109.9 g/eq and hydrolysable halogen content 1600 ppm.

The distillate contained mixture of isopropanol, epichlorohydrin and water and required fractionation for recovering and recycling epichlorohydrin and isopropanol.

Comparative Example 2 and 3

The procedure of comparative example 1 was repeated, except that the recovery solvent from previous batches of same process was used in Comparative Example 2 and Comparative Example 3 as shown in Table 2.

Examples 5 and 6

The procedure of Example 2 was repeated, except that the recovery epichlorohydrin from previous batches of same process was used in Examples 5 and 6 as shown in Table 2.

Examples 8 and 10

The procedure of Example 2 was repeated, except that mole ratio of water was varied as shown in Table 3.

Example 11 and 12

The procedure of Example 2 was repeated, except that reaction temperature was varied as shown in Table 4.

TABLE 1

Comparison mole ratio of epichlorohydrin/active hydrogen of amino phenol and isopropanol co-solvent process.

| | | Exp | | | | |
|---|---|---|---|---|---|---|
| | | Comparative Example 1 | 1 | 2 | 3 | 4 |
| | ECH/H (mole/mole) | 3.3 | 3.3 | 5 | 7 | 9 |
| | Water (% on PAP) | 0 | 70 | 70 | 70 | 70 |
| | ECH: IPA wt/wt | 80/20 | — | — | — | — |
| | NaOH/H (mole/mole) | 1.2 | 1.05 | 1.05 | 1.05 | 1.05 |
| | Rxn temp (° C.)/pressure | 55, atm | 55-60, vac | 55-60, vac | 55-60, vac | 55-60, vac |
| Waste water | COD (ppm) | 160000 | 8900 | 9320 | 9400 | 9800 |
| Crude solution | Solid content (%) | 25.4 | 51.8 | 30.6 | 22.8 | 17.2 |
| Product | EEW (gm/Eq) | 108.5 | 109.3 | 107.4 | 103.2 | 100.2 |
| | HyCl (%) | 0.195 | 0.084 | 0.065 | 0.075 | 0.043 |
| | Viscosity (cps) | 2897 | 3509 | 2875 | 2434 | 1672 |
| | Purity (%) | 68.7 | 65.5 | 68.2 | 73.2 | 77.2 |
| | Yield (%) | 98 | 96.3 | 96.5 | 95.3 | 96.2 |
| Recovery ECH | ECH (%) | 51.6 | 99.4 | 99.8 | 99.4 | 99.5 |
| | IPA (%) | 36.7 | — | — | — | — |
| | Water (%) | 11.5 | 0.45 | 0.22 | 0.56 | 0.42 |

In Comparative Example 1, the step involving washing of adduct to remove inorganic salt showed higher chemical oxygen demand (COD) levels in waste water, in comparison to experiment number 1 to 4 where only water was used in the reaction in place of polar protic organic solvent (isopropanol).

The result showed that excess of epichlorohydrin (5 moles) afforded the same level of viscosity as 28 cPs as compare with an isopropanol co-solvent process.

In Comparative Example 1, the water content in recovered epichlorohydrin and isopropanol mixture was much higher than experiments 1 to 4, due to presence of the polar protic organic solvent isopropanol. This restricts the reuse and recycling of recovered isopropanol and recovered epichlorohydrin without fractionation.

TABLE 2

Recovered epichlorohydrin and waste water quality comparison:

| | | | Exp | | | |
|---|---|---|---|---|---|---|
| | Comp. 1 | Comp. 2 | Comp. 3 | 2 | 5 | 6 |
| ECH/H (Mole/mole) | 3.3 | 3.3 (recovered and recycled from Comp. 1) | 3.3 (recovered and recycled from Comp. 2) | 5 | 5 (recovered and recycled from exp 2) | 5 (recovered and recycled from exp 5) |

TABLE 2-continued

Recovered epichlorohydrin and waste water quality comparison:

|  |  | Exp |  |  |  |  |  |
|---|---|---|---|---|---|---|---|
|  |  | Comp. 1 | Comp. 2 | Comp. 3 | 2 | 5 | 6 |
|  | Water (% on PAP) | 0 | 0 | 0 | 70 | 70 | 70 |
|  | ECH/IPA (wt./wt.) | 80/20 | 80/20 | 80/20 | — | — | — |
|  | NaOH/H (mole/mole) | 1.2 | 1.2 | 1.2 | 1.05 | 1.05 | 1.05 |
|  | Rxn temp (° C.) | 55, atm | 55, atm | 55, atm | 55-60, vac | 55-60, vac | 55-60, vac |
| Waste water | COD (ppm) | 110000 | 140000 | 160000 | 8600 | 9230 | 9150 |
| Crude solution | Solid content (%) | 25.4 | 25.4 | 25.4 | 30.6 | 29.8 | 30.5 |
| Product | EEW (gm/eq) | 108.5 | 108.9 | 109.3 | 107.4 | 107.1 | 107.3 |
|  | HyCl (ppm) | 0.195 | 0.283 | 0.354 | 0.065 | 0.054 | 0.062 |
|  | Viscosity (cps) | 2897 | 3240 | 3530 | 2875 | 3059 | 3126 |
|  | Purity (%) | 68.7 | 64.9 | 62.8 | 68.2 | 68.7 | 68.3 |
|  | Yield (%) | 98.2 | 97.3 | 97.5 | 96.5 | 96.3 | 96.8 |
| Recovery ECH | ECH (%) | 51.6 | 50.2 | 49.6 | 99.8 | 99.8 | 99.8 |
|  | IPA (%) | 36.7 | 40.3 | 42.2 | — | — | — |
|  | Water (%) | 11.5 | 12.9 | 12.4 | 0.22 | 0.24 | 0.2 |

In Examples 2, 5, and 6, when a polar protic organic solvent is not used in the process, the percent purity of recovered epichlorohydrin was high and remained stable in subsequent batches where recycled epichlorohydrin was used.

In waste water generated from the salt washing step from the organic layer after adduct formation, Comparative Examples 1, and 3 showed a rise in COD levels, when recovered epichlorohydrin, isopropanol mixture was used and recycled in subsequent batches.

In comparison, batches where water was used as a substitute for polar protic organic solvent, the COD level in washing water was quite stable.

TABLE 3

Comparison percent water in reaction solution.

| Exp |  | 8 | 9 | 10 | 2 |
|---|---|---|---|---|---|
| ECH/H (Mole/mole) |  | 5 | 5 | 5 | 5 |
| Water (% on PAP) |  | 0 | 20 | 40 | 70 |
| NaOH/H (mole/mole) |  | 1.05 | 1.05 | 1.05 | 1.05 |
| Rxn temp (° C.) |  | 55-60, vac | 55-60, vac | 55-60, vac | 55-60, vac |
| Waste water | COD ppm | 8700 | 8600 | 8900 | 8700 |
| Crude solution | Solid content (%) | 30.3 | 30.6 | 30.9 | 30.1 |
| Product | EEW (gm/eq) | 106.8 | 107.1 | 108.2 | 107.4 |
|  | HyCl (ppm) | 0.065 | 0.039 | 0.076 | 0.065 |
|  | Viscosity (cps) | 3010 | 2977 | 2987 | 2875 |
|  | Purity (%) | 69.2 | 70.5 | 70.2 | 68.2 |
|  | Yield (%) | 87.5 | 95.8 | 96.2 | 96.5 |
| Recovery ECH | ECH (%) | 99.8 | 99.8 | 99.8 | 99.8 |
|  | Water (%) | 0.2 | 0.2 | 0.2 | 0.2 |

When the percentage of water in the formation of the halohydrin adduct was increased from 20% and 70%, no significant difference in the product yield was observed, however the physical appearance of adduct solution at a lower percentage of water was thick due to a higher amount of suspended solids in solution than when 70% water was used (Example 2), in which the adduct solution viscosity was low due to less suspended solids.

A higher amount of water (70%) was found to promote adduct formation and prevent precipitation of adduct in the solution, but does not impact on overall yield of N,O-triglycidyl compounds at the end of reaction.

TABLE 4

Comparison of reaction temperature.

| Exp |  | 11 | 2 | 12 |
|---|---|---|---|---|
| ECH/H |  | 5 | 5 | 5 |
| Water (% on PAP) |  | 70 | 70 | 70 |
| NaOH/H |  | 1.05 | 1.05 | 1.05 |
| Rxn temp (° C.) |  | 45-50, vac | 55-60, vac | 65-70, vac |
| Waste water | COD ppm | 8500 | 8600 | 8350 |

TABLE 4-continued

Comparison of reaction temperature.

| Exp |  | 11 | 2 | 12 |
|---|---|---|---|---|
| Crude solution | Solid content (%) | 30.8 | 30.2 | 30.6 |
| Product | EEW (gm/eq) | 108.3 | 107.1 | 109.2 |
|  | HyCl (ppm) | 0.754 | 0.039 | 0.062 |
|  | Viscosity (cps) | 3123 | 2977 | 3457 |

TABLE 4-continued

Comparison of reaction temperature.

| Exp | 11 | 2 | 12 |
|---|---|---|---|
| Purity (%) | 65.3 | 70.5 | 65.2 |
| Yield (%) | 96.2 | 95.8 | 96.0 |

At a reaction temperature <50° C., the amount of epichlorohydrin was observed to be high, which indicated incomplete cyclisation; however, at a temperature >60° C., the hydrolysable chlorine value decreased, but the overall purity of N,O-triglycidyl compounds also decreased. Although not wishing to be bound by any particular theory, this result indicated byproduct formation due to secondary reactions.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for producing a triglycidyl aminophenol from at least one aminophenol and at least one epihalohydrin, comprising the steps of:
   (i) reacting at least one aminophenol with at least one epihalohydrin in the presence of a polar solvent present in an amount in the range of from 20% to 70% by weight based on the weight of the at least one aminophenol and in the absence of an organic solvent to produce a halohydrin compound in a reaction mixture;
   (ii) reacting the halohydrin compound in the reaction mixture with at least one alkali metal hydroxide in the absence of a co-catalyst to form the triglycidyl aminophenol;
   (iii) removing unreacted epihalohydrin from the reaction mixture;
   (iv) adding an organic solvent and an aqueous solvent to the reaction mixture to form an organic layer and an aqueous layer;
   (v) isolating the organic layer;
   (vi) washing the organic layer with water;
   (vii) isolating the organic layer by removing the water by phase separation; and
   (viii) recovering the organic solvent from the organic layer to provide the triglycidyl aminophenol:
   wherein the triglycidyl aminophenol is at least one compound formula I and formula II:

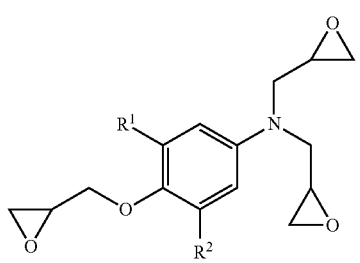

(I)

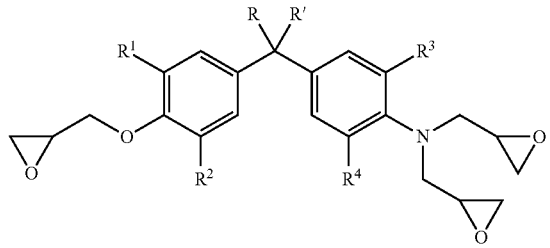

(II)

wherein:
R and R' are each independently selected from the group consisting of hydrogen, $C_1$-$C_6$ alkyl, phenyl, cyclohexyl and cyclopentyl; and
$R^1$, $R^2$, $R^3$, and $R^4$ are each independently selected from the group consisting of hydrogen, halogen, and $C_1$-$C_6$ alkyl;
mixtures thereof and salts thereof:
wherein the aminophenol is at least one compound of formula III and formula IV:

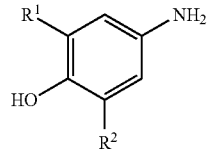

(III)

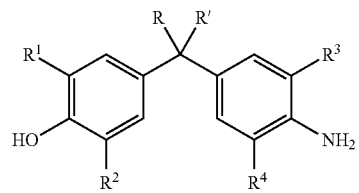

(IV)

wherein:
R and R' are each independently selected from the group consisting of hydrogen, $C_1$-$C_6$ alkyl, phenyl, cyclohexyl and cyclopentyl; and
$R^1$, $R^2$, $R^3$, and $R^4$ are each independently selected from the group consisting of hydrogen, halogen, and $C_1$-$C_6$ alkyl;
mixtures thereof and salts thereof, and wherein the polar solvent is water.

2. The method of claim 1, wherein the epihalohydrin is at least one compound of formula V:

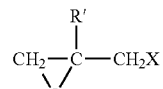

(V)

wherein:
R' is hydrogen; and
X is selected from the group consisting of chlorine and bromine; and mixtures thereof.

3. The method of claim 1, wherein step (iii) further comprises removing the polar solvent.

4. The method of claim 1, wherein the organic solvent of step (iv) is isolated and recycled without any additional purification.

5. The method of claim 1, wherein in step (iii), the epihalohydrin is free of hydrolyzed byproducts.

6. The method of claim 1, wherein in step (iii), the epihalohydrin is removed from the reaction mixture by distillation.

7. The method of claim 1, wherein in step (viii), the organic solvent is recovered from the organic layer by distillation.

8. The method of claim 1, wherein in step (vi), the organic layer is washed once with water.

9. The method of claim 1, wherein in step (vi), the amount of water used for washing the organic layer is between about 0.5 mol to about 5 mol per mole of the at least one aminophenol.

10. The method of claim 1, wherein the organic solvent is selected from the group consisting of an aromatic hydrocarbon and a cyclic fatty hydrocarbon.

11. The method of claim 1, wherein the organic solvent is toluene or m-xylene.

12. The method of claim 1, wherein steps (i)-(viii) are carried out in a batch process.

13. The method of claim 12, wherein at least a portion of the organic solvent recovered in step (viii) is used in step (iv) of a subsequent batch process.

14. The method of claim 12, wherein at least a portion of the epichlorohydrin removed in step (iii) is used in step (i) of a subsequent batch process.

15. The method of claim 1, wherein the amount of at least one epihalohydrin is about 3 to about 5 moles per active hydrogen of the at least one aminophenol.

16. The method of claim 1, wherein, in step (iii), the unreacted epihalohydrin is removed under reduced pressure.

17. The method of claim 16, wherein the epihalohydrin is removed at a temperature below 90° C.

18. The method of claim 1, wherein the chemical oxygen demand (COD) of the polar solvent is less than about 10,000 ppm.

19. The method of claim 1, wherein the triglycidyl aminophenol is produced in a yield greater than about 98%.

20. The method of claim 1, wherein the triglycidyl aminophenol has a hydrolysable halogen content less than about 400 ppm.

* * * * *